United States Patent
Bishop et al.

(10) Patent No.: US 9,113,091 B2
(45) Date of Patent: Aug. 18, 2015

(54) HIGH SPEED AUTOFOCUS SYSTEM

(71) Applicant: Stella Alliance, LLC., Needham, MA (US)

(72) Inventors: Robert Bishop, Newton, MA (US); Timothy Pinkney, Cambridge, MA (US)

(73) Assignee: Stella Alliance, LLC, Needham, MA (US)

( * ) Notice: Subject to any disclaimer, the term of this patent is extended or adjusted under 35 U.S.C. 154(b) by 0 days.

(21) Appl. No.: 13/930,520

(22) Filed: Jun. 28, 2013

(65) Prior Publication Data

US 2014/0104409 A1 Apr. 17, 2014

Related U.S. Application Data

(63) Continuation of application No. 13/651,583, filed on Oct. 15, 2012.

(60) Provisional application No. 61/547,916, filed on Oct. 17, 2011.

(51) Int. Cl.
*H05K 13/08* (2006.01)
*H04N 5/235* (2006.01)
*H04N 7/18* (2006.01)
*G01N 21/64* (2006.01)

(52) U.S. Cl.
CPC ......... *H04N 5/2356* (2013.01); *G01N 21/6456* (2013.01); *H04N 7/18* (2013.01); *G01N 2021/6463* (2013.01)

(58) Field of Classification Search
CPC .......... G02B 13/00; G02B 15/00; G03B 9/22; G03B 9/24; H04N 7/18; G01N 21/6456; G01N 2021/6463

USPC .......................................................... 348/87
See application file for complete search history.

(56) References Cited

U.S. PATENT DOCUMENTS

| | | | |
|---|---|---|---|
| 5,646,733 A * | 7/1997 | Bieman | 356/604 |
| 5,672,885 A | 9/1997 | Allen et al. | |
| 6,014,209 A | 1/2000 | Bishop | |
| 6,055,055 A * | 4/2000 | Toh | 356/609 |
| 6,091,488 A | 7/2000 | Bishop | |
| 6,242,756 B1 * | 6/2001 | Toh et al. | 250/559.34 |
| 6,324,298 B1 | 11/2001 | O'Dell et al. | |

(Continued)

FOREIGN PATENT DOCUMENTS

| | | |
|---|---|---|
| JP | 62-144008 | 6/1987 |
| JP | H6-68442 | 8/1994 |

(Continued)

OTHER PUBLICATIONS

PCT/US2012/060480 International Search Report and Written Opinion.

(Continued)

*Primary Examiner* — Tung Vo
(74) *Attorney, Agent, or Firm* — George A. Herbster

(57) ABSTRACT

A method and apparatus for optimizing high-speed optical inspection of parts using intelligent image analysis to determine optimal focus using high numerical aperture (NA) optics, achieve a superior signal-to-noise ratio, resolution, and inspection speed performance with very limited depth of field lenses.

18 Claims, 17 Drawing Sheets

(56) References Cited

U.S. PATENT DOCUMENTS

| | | |
|---|---|---|
| 6,674,058 B1 | 1/2004 | Miller |
| 6,762,609 B2 | 7/2004 | Alanen et al. |
| 7,015,445 B2 * | 3/2006 | Bishop ................. 250/201.4 |
| 7,109,464 B2 * | 9/2006 | Cartlidge et al. ........ 250/208.1 |
| 7,196,300 B2 * | 3/2007 | Watkins et al. ........... 250/201.2 |
| 7,247,825 B2 * | 7/2007 | Sonksen et al. ........... 250/201.3 |
| 7,355,691 B2 * | 4/2008 | Yamaguchi et al. ....... 356/237.4 |
| 7,382,457 B2 * | 6/2008 | Kiraly ................... 356/430 |
| 7,719,669 B2 | 5/2010 | Matsui et al. |
| 7,728,966 B2 * | 6/2010 | Kim et al. ............... 356/237.2 |
| 8,456,522 B2 * | 6/2013 | Olson et al. ............. 348/80 |
| 2002/0036769 A1 | 3/2002 | Shimoda et al. |
| 2003/0053676 A1 | 3/2003 | Shimoda et al. |
| 2003/0164440 A1 | 9/2003 | Czarnetzki et al. |
| 2004/0183902 A1 | 9/2004 | Bishop |
| 2007/0090189 A1 * | 4/2007 | Suwa et al. ............. 235/454 |
| 2009/0290781 A1 * | 11/2009 | Yannick et al. ........... 382/141 |
| 2011/0001818 A1 | 1/2011 | Hur et al. |

FOREIGN PATENT DOCUMENTS

| | | |
|---|---|---|
| JP | 2000-266691 | 3/1999 |
| JP | 11-108615 | 4/1999 |
| JP | 11-223607 | 8/1999 |
| JP | 2002-236003 A | 8/2002 |
| JP | 2004-144610 A | 5/2004 |
| JP | 2007-327891 A | 12/2007 |
| WO | 2004-061430 | 7/2004 |
| WO | 2010-120231 | 10/2010 |

OTHER PUBLICATIONS

International Preliminary Report on Patentability of Mar. 18, 2014, PCT/US12/60480.

* cited by examiner

HIGH SPEED AUTOFOCUS SYSTEM

CROSS REFERENCE TO RELATED APPLICATION

This application is a continuation of co-pending U.S. patent application Ser. No. 13/651,583 filed Oct. 15, 2012 which is a non-provisional of Ser. No. 61/547,916 filed Oct. 17, 2011.

BACKGROUND OF THE INVENTION

1. Field of Invention

This invention generally relates to the optical inspection of electronic parts and more specifically to an autofocus system for use in such optical inspection.

2. Description of Related Art

Optical inspection of electronic parts such as such as wafers, circuit boards, flat panel displays, multi chip modules, and high-density electronic packages requires the use of high resolution optics to detect small defects in the part. In addition the high resolution optics part must be kept in focus during the entire inspection to see the defects. FIG. 1 is the example of a part 1-1 with variations in surface height Z in both the scanning direction 1-2 and in an orthogonal direction relative to the scanning direction. Newly introduced circuit boards with embedded dies are examples of such parts and are recognized as being difficult to image because the surfaces being imaged are subject to height variations caused by the embedded die or circuits placed on and between the substrate layers and the recognized characteristic that the substrate itself will warp.

FIG. 1 is helpful in understanding problems that exist when prior art apparatus is required to image defects in various parts. In the prior art, a camera, not shown, scans over the surface of a part in a scanning direction 1-2. As the scan images an area such as shown in FIG. 1 which is transverse to the scanning direction 1-2, the image taken by the camera must be in focus. The part shown in FIG. 1 has a range of height variations, shown by arrows 1-3 that must be within the depth of field of the camera optics. With prior art imaging apparatus, a particular focus point selected for the camera could arbitrarily be at the top 1-5 of or the bottom 1-6 of the part or at any intermediate position. Given this, optics design of the imaging optics sets the required depth of field, preferably twice the distance between the top 1-5 and bottom 1-6 of the part as shown by arrows 1-7 and 1-8 that depict a depth that will cover the range of height variations. However, as known and described in greater detail later, the depth of field for an optics system also determines the resolution of the image. Such resolutions often limit image quality that will prevent the detection of small defects in the part.

To inspect the part for defects a camera is frequently used to scan the part in a serpentine pattern as illustrated by the contiguous strips A through E in FIG. 2. The width of the camera's field of view is represented by rectangle 2-1. Various techniques have been described in the art to maintain focus during such inspections. U.S. Pat. No. 7,015,445 to Bishop for "Method for Optimizing Inspection Speed in Low, and Fluorescent Light Applications without Sacrificing Signal to Noise Ratio, Resolution, or Focus Quality" describes the use of a triangulation sensor to maintain a constant distance between the imaging optics and part as the part is scanned. FIG. 3 shows a wavy part 3-1 at an incline θ, imaging optics 3-2 and an imaging camera 3-3. As the part is scanned the imaging optics 3-2 and imaging camera 3-3 are raised and lowered as a unit to keep the surface of the part within the optical depth of field 3-4 of the imaging optics. Conceptually the part, the optics, or the combination of the optics and camera can be moved to maintain focus.

FIG. 4 shows the use of a triangulation sensor with an optical source 4-1, illumination beam 4-2 and position sensor 4-3. The triangulation sensor scans ahead of the camera as indicated by arrow 4-4. The position at which optical beam 4-5 hits the position sensor indicates the distance to the part 4-6. In this FIG. 4, the imaging camera optics has a depth of field (DOF) 4-7. This distance measurement is used in a feedback loop to mechanically move either the imaging optics or the part relative to each other to maintain focus. FIG. 5 shows how the position of the beam onto position sensor 5-1 moves as a function of the distance to the part. Three surfaces at different distances represented by surfaces 5-3, 5-4, and 5-5, are projected onto sensor 5-1 at positions 5-3', 5-4', and 5-5' respectively. These distance measurements are used in a feedback loop mechanically to move either the optical head or the part as a function of the measured height to maintain focus.

There are two limitations to these focusing methods. First, if an illumination beam 4-2 in FIG. 4 hits the part at a material boundary the distance measurement may be incorrect. Referring to FIG. 6 and specifically to FIG. 6A, when optical beam 6-1 from the triangulation sensor hits highly reflective material 6-2, the entire illumination spot 6-3 sits on material 6-2. The image of this spot creates a symmetrical shaped beam 6-4 on sensor 6-5. If the material beneath the sensor now changes, as the part is scanned to one with a lower reflectivity, represented by 6-6 in FIG. 6B, a lower intensity spatially symmetrical spot represented by 6-7 is projected onto sensor 6-5. So long as projected spots 6-7 and 6-4 are spatially symmetrical, the center of mass of the spots, which represents the distance to the part, will be the same and the correct focus distance will be calculated. If, however, the illumination spot 6-3 falls on a material boundary as in FIG. 6C, it is spread between highly reflective material 6-2 and lower reflective material 6-3. In this event, the spot projected onto the sensor will not be symmetrical and the distance to the part will be incorrectly calculated to be at position 6-8 when the correct distance should be at position 6-7 because the center of mass of the spot no longer represents the correct distance to the part Second, in FIG. 7 an imaging camera 7-1 with imaging optics 7-2 moves in the focus direction along a Z axis 7-3 to maintain constant distance to the surface of part 7-4 while focus distance is adjusted dynamically as the part is scanned in the Y direction. Focus distance for the entire imaging camera is based on a series of single point measurements along a narrow line in the direction of scan. No measurements are taken perpendicular to the direction of scan. This implies that across the width of the camera, or width of each scanned strip A-E shown in FIG. 2, all features on the surface must lie within the optical depth of field of the imaging optics indicated by arrow 3-4 in FIG. 3. As will be apparent any feature not within the depth of field will be out of focus.

As the part is scanned, the focus measurement unit may pass over high or low features in the part. Some focus distances may be calculated based on the distance to a high feature while other focus distances may be calculated based on the distance to a low feature. This implies that the optical depth of field of the imaging optics must be sufficiently large to insure proper focus regardless of whether a high or low feature was beneath the focus measurement unit at the time when the focus measurement was calculated. Calculating focus based only on measurement values along a line in the direction of scan will have this limitation, regardless of how many measurements are acquired, how fast the calculations are computed, the specific method of measurement or type of measurement device. A preferred device is a single point triangulation sensor; single-point confocal sensors, single point capacitive sensors and others may be substituted depending upon the performance criteria to be provided by the inspection apparatus.

Table 1 is a list of commercially available lenses from the Zeiss Corporation. The table lists the depth of focus, numerical aperture, resolving power, light collection coefficient, light collection cone angle, working distance magnification and part number for each lens.

TABLE 1

Commercially Available Objective Lenses From Zeiss

| Magnification/ pixel size (microns) | Zeiss Part Number | Numerical Aperture (NA) | Light Collection Coefficient (NA²) | Light Collection Cone Angle (degrees) $\theta = 2\times\sin^{-1}(NA)$ | Resolving Power for $\lambda = 0.55$ (Microns) $\frac{\lambda}{2\times NA}$ | Depth of Focus $\lambda = 0.55$ (Microns) $\frac{\lambda}{2\times NA^2}$ | Working Distance (WD) |
|---|---|---|---|---|---|---|---|
| 1.25x/10.4 | 442300 | 0.035 | 0.0012 | 4.0 | 7.8 | 229 | 3.9 mm |
| 2.5x/5.2 | 442310 | 0.075 | 0.0056 | 8.6 | 3.6 | 49 | 9.4 mm |
| 5x/2.6 | 440320 | 0.15 | 0.0225 | 17 | 1.8 | 12.2 | 13.6 mm |
| 5x/2.6 | — | 0.25 | 0.0625 | 29 | 1.1 | 4.4 | — |
| 10X/1.3 | 442832 | 0.25 | 0.0625 | 29 | 1.1 | 4.4 | 12.7 mm |
| 10X/1.3 | 442330 | 0.30 | 0.0900 | 35 | 0.9 | 3.1 | 5.7 mm |
| 20X/0.65 | 442840 | 0.40 | 0.1600 | 47 | 0.7 | 1.7 | 9.8 mm |
| 10X/1.3 | 440135 | 0.50 | 0.2500 | 60 | 0.5 | 1.1 | 2.0 mm |
| 20X/0.50 | 442340 | 0.50 | 0.2500 | 60 | 0.5 | 1.1 | 1.4 mm |

For current focus tracking technology to properly function the depth of focus of the imaging optics, indicated as arrow 8-1 in FIG. 8, must be sufficiently large to guarantee focus for all the possible features heights that may be used to calculate the focus distance. It is important to note that FIG. 8 represents the surface of the part in the X axis which is perpendicular to the direction of mechanical scan. FIG. 8 also represents the image projected onto the long axis of a linear CCD scan camera as represented by block 2-1 in FIG. 2. Unfortunately requiring this large depth of field seriously limits the spatial resolution and defect detection capabilities of the inspection system. More specifically, the optical depth of focus (DOF) is given by the equation:

$$DOF = \frac{\lambda}{2NA^2}$$

and Resolution is given by the equation:

$$Resolution = \frac{\lambda}{2NA}$$

where:
$\lambda$=Wavelength of light imaged onto the camera, and
NA=numerical aperture of the imaging optics As known and demonstrated by the foregoing relationships, large depth of focus (DOF) requires a small numerical aperture (NA) while high resolution requires a large numerical aperture. As (NA) becomes smaller, the level of light reaching the imaging camera, also decreases and this impacts the contrast in the final image. These criteria impose limitations on the inspection of parts that can prevent the construction of imaging optics with both a large depth of focus and a high resolution. As will be apparent, if the part being inspected must stay in focus, current inspection systems sacrifice the resolution of the imaging optics which thereby inherently limits the ability to detect small defects.

Note that the 1.25× lens with an NA of 0.035 has a depth of focus of 229 microns whereas the 20× lens with an NA of 0.50 only has a depth of focus of 1.1 microns. Unfortunately, unless all the features in the field of view of the inspection camera vary in height less than 1.1 microns, the 20× 0.5 NA lens cannot be used to inspect the part. Therefore many inspection systems are forced to use low NA optics to maintain focus and are unable to inspect very small features that require high magnification and high resolution.

SUMMARY

Therefore, it is an object of this invention to provide a method and apparatus for providing high-speed autofocusing that enables features on a part to be identified based on their height and focused upon during inspection thereof.

Another object of this invention is to provide high-speed autofocusing that enables features on a part to be identified based on their height and focused upon during inspection thereof with imaging optics that provides sufficiently high resolution and depth of field to detect small features and defects on the part.

In accordance with one aspect of this invention a method for inspecting a part takes a plurality of images of different image fields of the part with an imaging camera having imaging optics with a fixed resolution and depth of field. The surface of the part is characterized by height variations within a given image field and by the image optics depth of field such that focusing on any point in the given image field does not guarantee that the entire corresponding image will be in focus. The height of the part surface is sampled at multiple positions in the given image field with a sample spacing that is sufficiently small to determine the range of height variations of the surface in the image field. A focus position for the imaging optics for each image is determined based upon the sampled heights for the given image field such that all surfaces of interest in the image field will be within the depth of field for the imaging optics. The imaging optics is moved to the focus position for the given image field whereby the image will be in focus across the image field.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

An intelligent autofocus system in accordance with this invention analyzes the surface heights of the features in a part in real time as the part is scanned to create an optimally focused image for inspection of the desired features in the part. It can be implemented as a stand-alone unit placed in advance of the inspection camera or incorporated into a real time through the lens inspection system.

Figure 9:
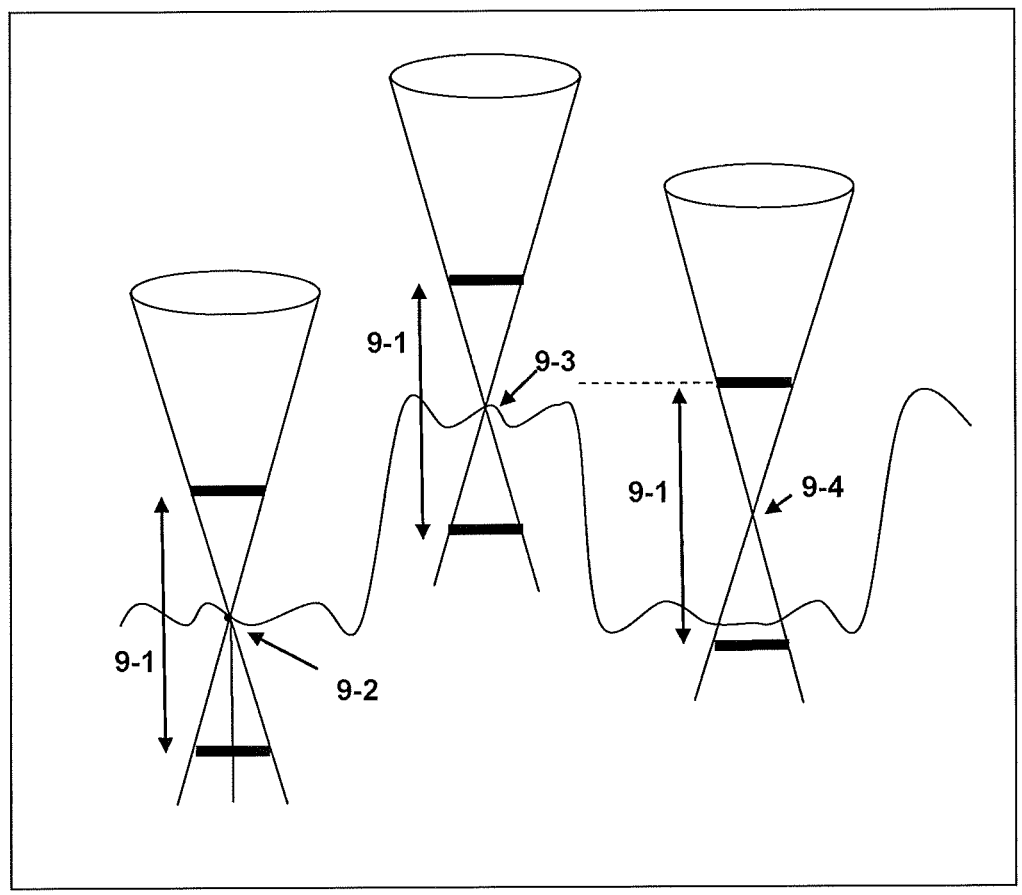

One feature of this invention is the ability to dynamically compute and mechanically track the optimal focal plane for a given imaging optics during inspection of the part. As one example, consider FIG. 9 which shows imaging optics with depth of field indicated by arrow 9-1. Using the prior art technology, the imaging optics would either be focused on the lower surface 9-2 or upper surface 9-3. If the imaging optics were focused on lower surface 9-2, the top surface 9-3 would be out of focus. Likewise, if an imaging optics were focused on top surface 9-3, the lower surface would be out of focus. As the part is scanned, both surfaces may appear beneath the prior art focusing system. At some positions the top surface may be in focus, and at other positions the lower surface may be in focus, so there is no way of knowing which surface will be in focus at any given time as the part is scanned. This makes high resolution inspection nearly impossible. One feature of this invention is to provide a method of intelligently identifying the heights of both surfaces, to determine an optimal focus plane spaced between the two surfaces indicated by position 9-4 that will enable both surfaces to remain within the optical depth of field of the given objective during the inspection of the part.

Figure 10:
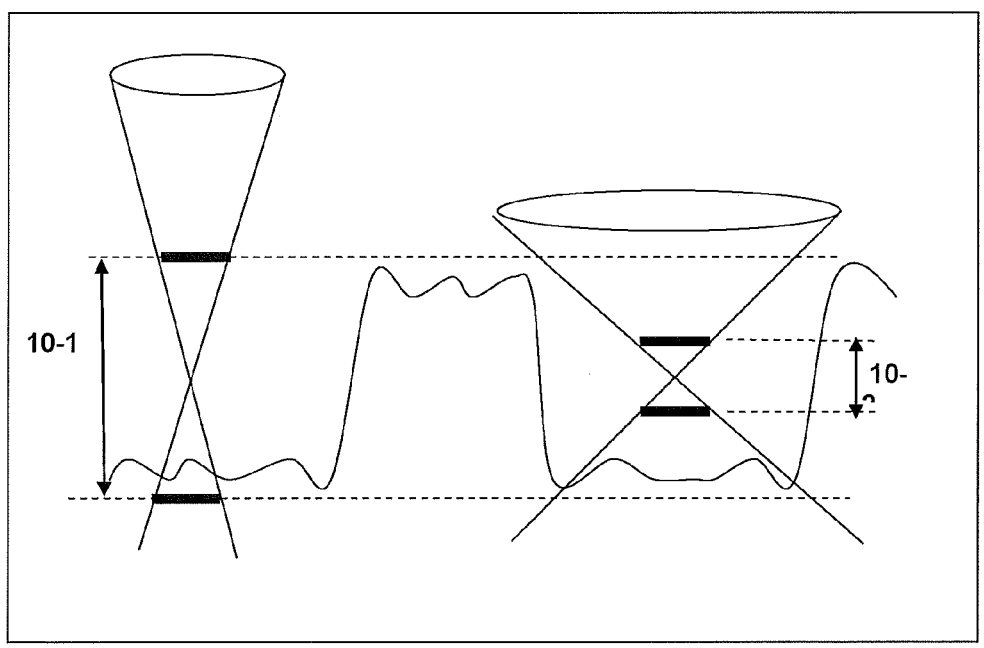
Figure 11:
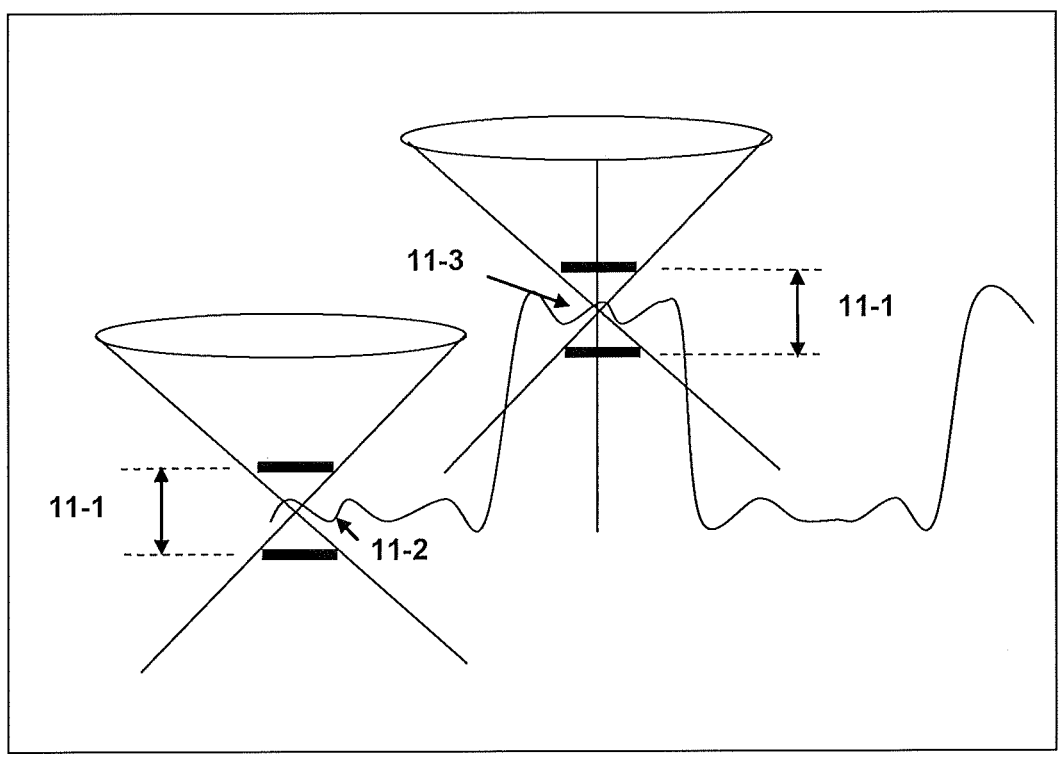

In many applications the resolution required for inspection is so high and depth of field is so low or the height difference between features is so large such that is not possible to keep all surfaces in focus simultaneously as the part is inspected. This is illustrated in FIG. 10 which shows a medium resolution lens depth of field 10-1 and higher resolution lens with lower depth of field 10-2. Referring to FIG. 11, if such a part is to be inspected with high resolution, low depth of field optics 11-1, it must be decided prior to scanning the part whether the specific scan will inspect the lower surface 11-2 or the upper surface 11-3. In applications such as wafers, high density interconnect modules, and printed circuit boards, the part consists of metal conductors placed onto a substrate. The metal conductors, which form the top surface, are the primary features of interest to be inspected for defects. This invention provides means to dynamically compute the height of the metal upper surface 11-3 and keep it in focus as the part is scanned.

Figure 12A:
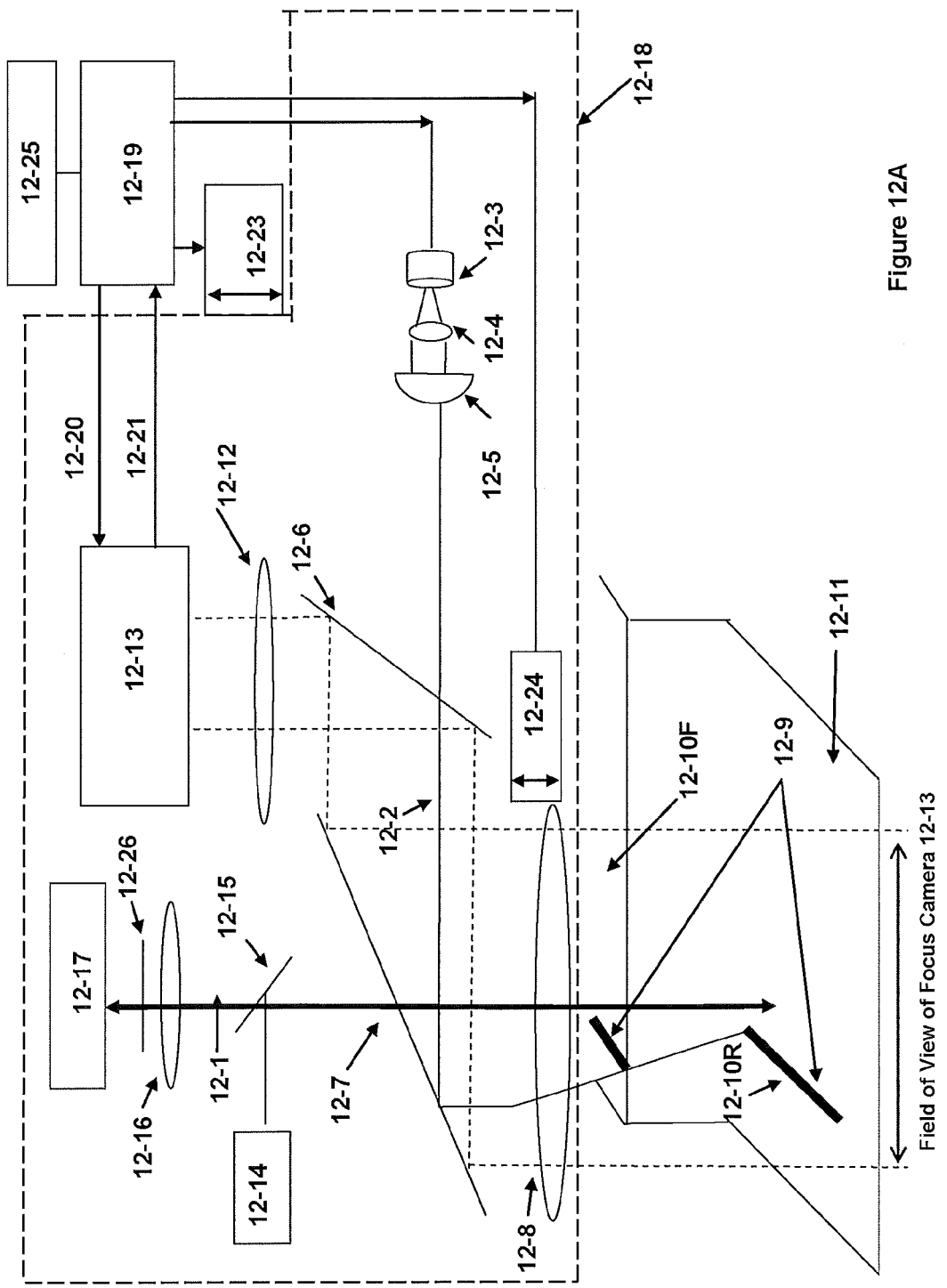
FIGS. 12A and 12B are block diagrams of two embodiments of this invention.

Referring to FIG. 12A, as a part is scanned and inspected in visible light (350 nm to 700 nm) as indicated by arrow 12-1, an infrared beam 12-2 (780 nm, for example) passes through the optics and is used to maintain focus. The infrared beam from a focus illumination source 12-3 comprising a laser diode, solid state LED, or any other light-emitting device is collimated by lens 12-4. The collimated light passes through a cylinder lens 12-5 and beam splitter 12-6 to reflect from a dichroic mirror 12-7 through a lens 12-8 to project a line 12-9 onto the part 12-11. This focused beam is positioned off axis to illuminate only half of the optical field. So the infrared beam is imaged onto the part at an angle θ, relative to the surface of the part as illustrated in FIG. 12A. Due to the surfaces being at different heights in the part, one side of the beam projects onto an upper surface 12-10 at a given position in X and the other side of the beam projects onto a lower surface 12-11 at a different position in X. Light rays from the line image projected onto these surfaces then pass back through lens 12-8, reflect from dichroic mirror 12-7 and beam splitter 12-6 and then are focused by a lens 12-12 onto a positioning or height measurement camera 12-13.

In one embodiment the entire focus path operates in the infrared wavelength (780 nm, as an example) so this focus light does not interfere with the visible light inspection path that operates in the range of (350-700) nm. The visible light path consists of an illumination source 12-14 and light from that source 12-14 reflects from a beam splitter 12-15 to pass through dichroic filter 12-7 which passes the visible light and reflects the infrared light. This visible beam then passes through broadband imaging lens 12-8, which also passes both visible and near infrared light. The reflected visible light image then returns through lens 12-8, passes through dichroic filter 12-7 and beam splitter 12-15 to be imaged by lens 12-16 onto inspection camera 12-17. Other means may be used to produce light 12-14 used by inspection camera 12-17. For example, some parts to be inspected may have an organic single layer, an organic non-transparent layer, or very opaque organic material, in which only the top metal surface needs to be inspected. In such cases there is no interference or image artifacts caused from lower layer images, which could confuse the autofocus apparatus. In such an application an appropriate laser could be substituted for the source 12-3 thereby to cause the top surface to fluoresce. Beam splitter 12-15 would be replaced by a dichroic mirror to reflect the laser and permit fluorescence returning from the part to reach inspection camera 12-17. A laser blocking filter 12-26 to allow only the returning fluorescing rays and also to block any laser illumination light from reaching the inspection camera 12-17 is also placed in front of camera 12-17. This fluorescing image may produce better contrast of the conductors on the organic surface.

Figure 13:
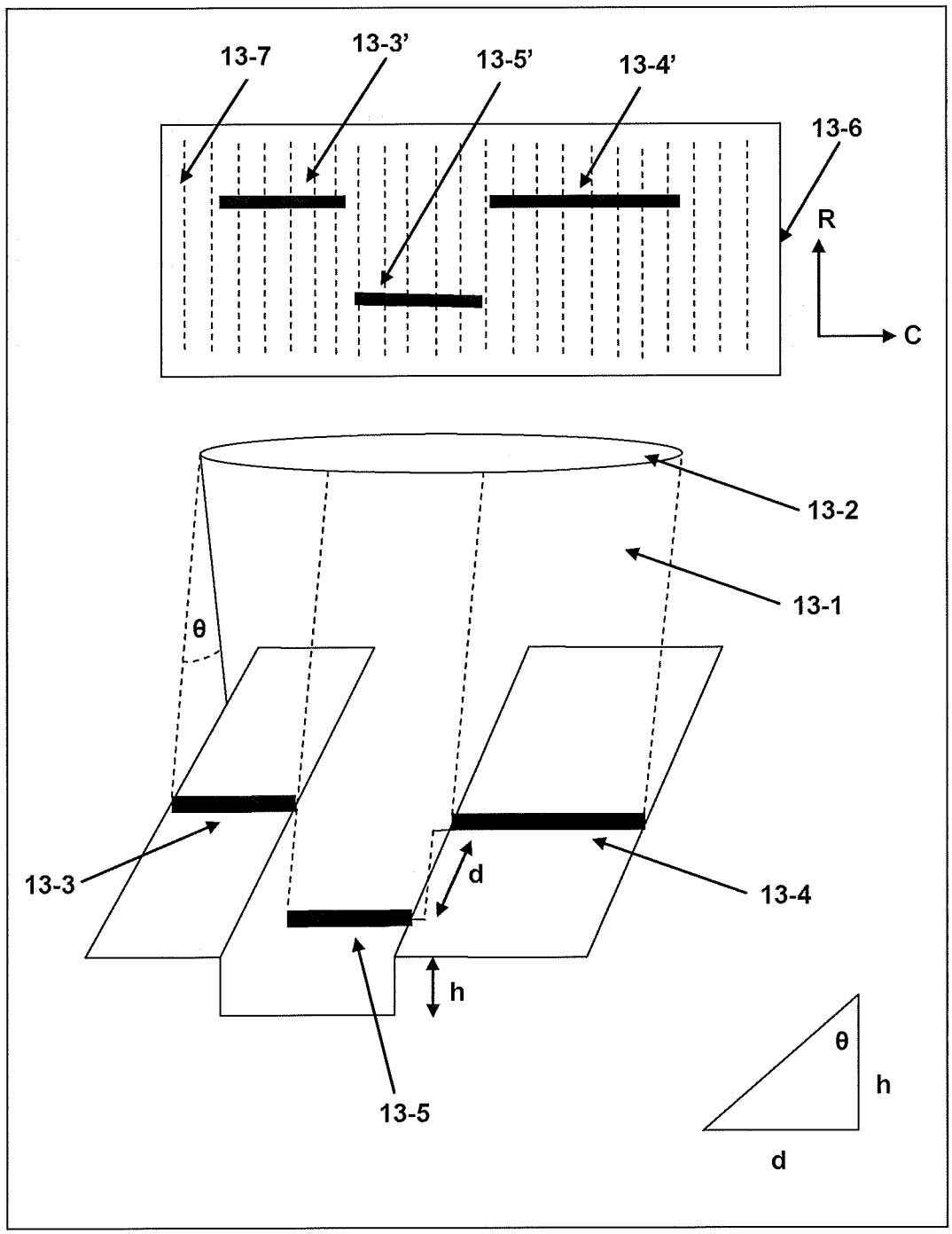
FIGS. 13 and 14 are useful in understanding the operation of the first embodiment of the apparatus in FIG. 12A.

Referring to FIG. 13 and to explain in greater detail how the autofocus system operates, consider a line-shaped beam 13-1, emanating from optical lens 13-2 that illuminates a part at an angle θ relative to the surface of the part as shown in FIG. 13. The position that the line hits the top surfaces 13-3 and 13-4 will be offset in the Y direction from the position that the line hits the lower surface 13-5 by a distance d such that:

$$d = h \tan(\theta)$$

where:
h=height difference between the surfaces, and
θ=angle of the illumination beam relative to a line perpendicular to the surface.

Figure 12B:
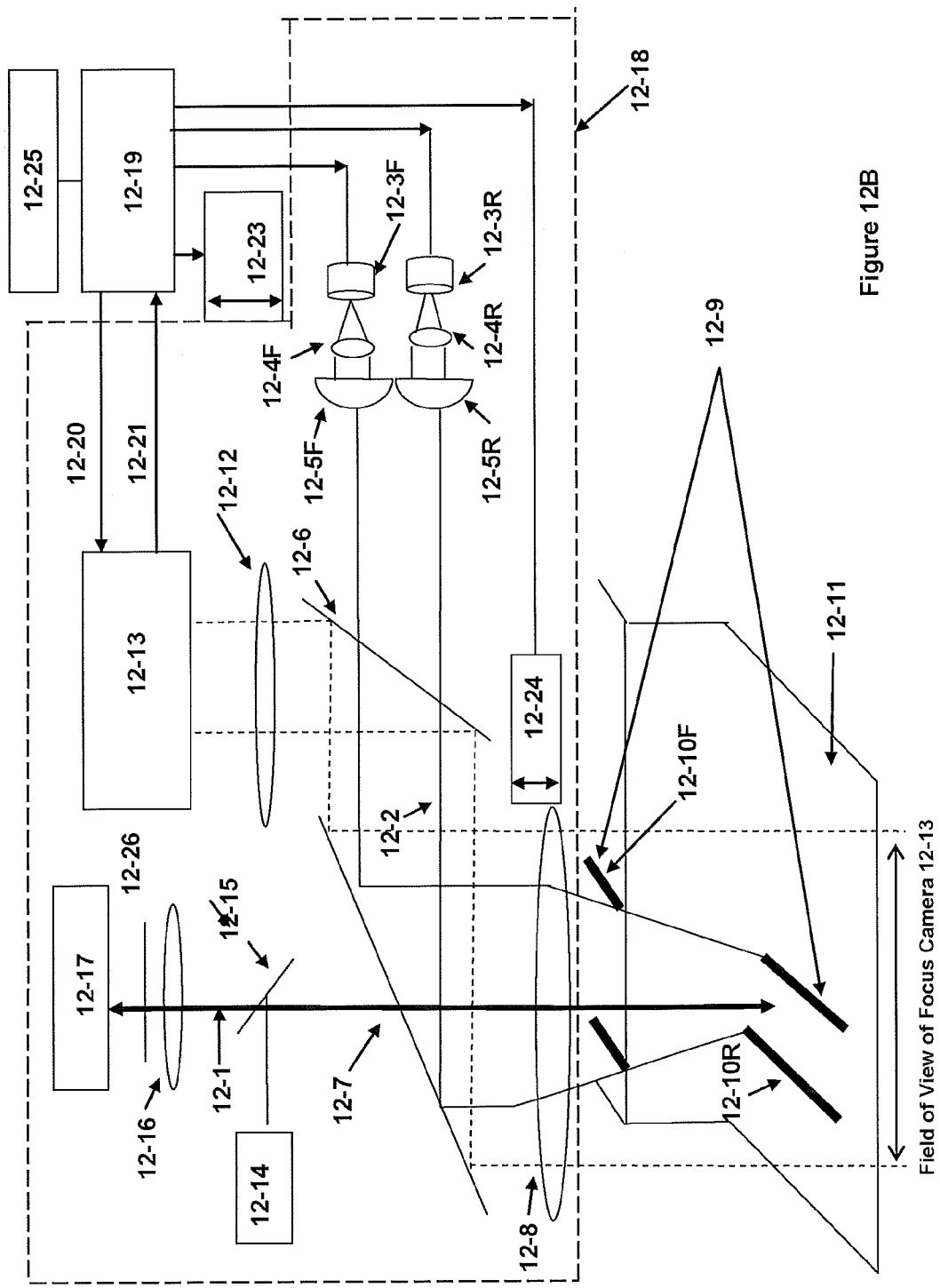

Lens 13-2 in FIG. 13 corresponds to lens 12-8 in FIG. 12A or 12B. The image of the projected line pattern is projected onto camera 13-6 which corresponds to the height measurement camera 12-13 in FIGS. 12A and 12B. Lines 13-3, 13-4, and 13-5 are imaged onto camera 13-6 as lines 13-3', 13-4', and 13-5' respectively.

Camera pixels are organized into rows R and columns C. Arrow 13-7 points to the left-most column in the camera 13-6. The row R position of the data on camera 13-6 indicates the height of the different surfaces on the part. By intelligently analyzing the image, and more specifically the row R position of the data, one can determine the location of the top and bottom surfaces and mechanically drive the focusing lens, camera and optics to track the desired surface.

Figure 14:
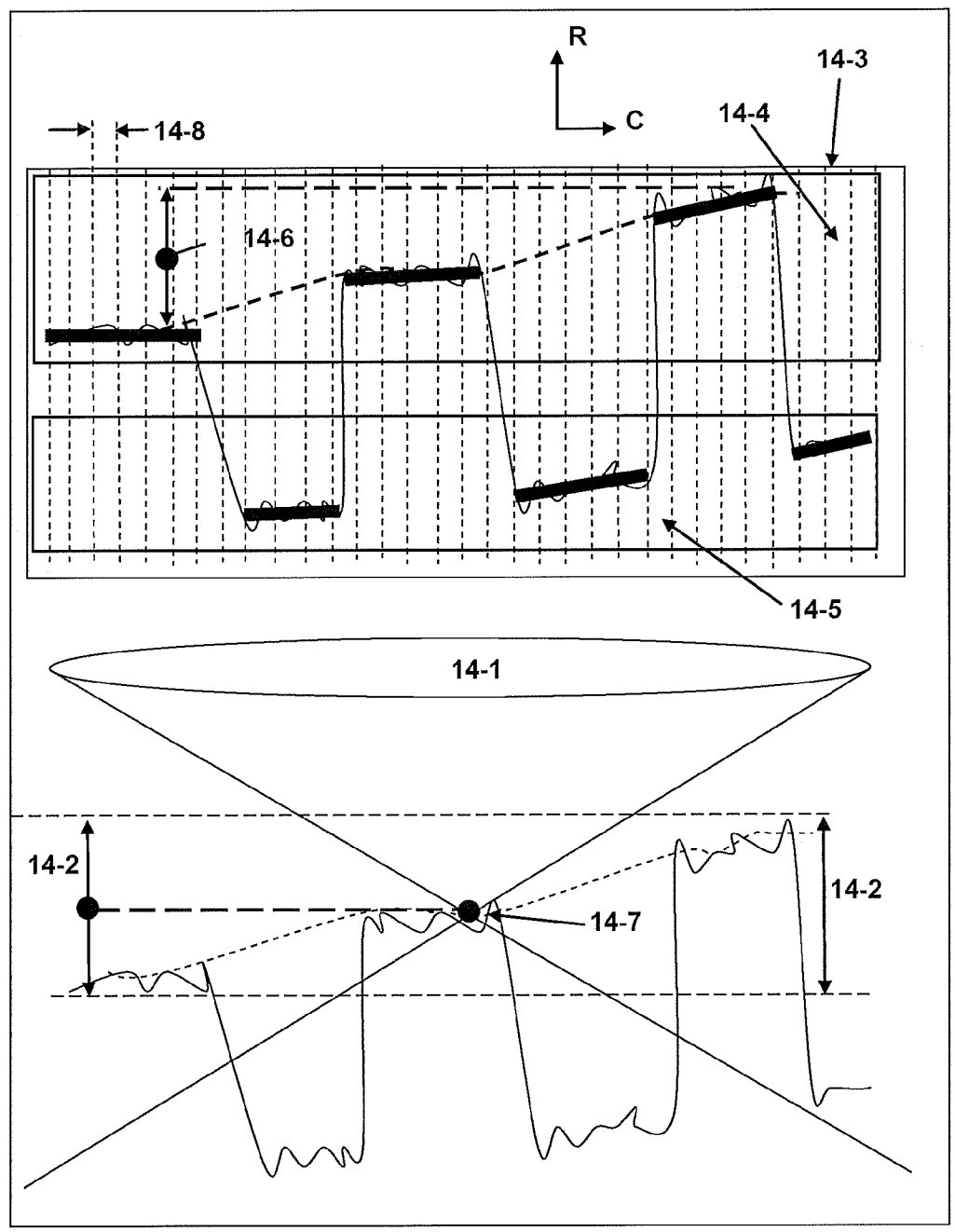

As an example, consider a high resolution, high NA optical lens 14-1 in FIG. 14 with corresponding shallow depth of field 14-2. The image of the projected line pattern is imaged onto camera 14-3. The camera field may be divided into upper region 14-4 and lower region 14-5. The row positions R of the information in upper region 14-4 corresponds to the height of the upper surfaces on the part. The row positions R of the information in lower region 14-5 correspond to the heights of the lower surfaces on the part.

If the goal is to keep the top surface in focus, then only data in upper region 14-4 is analyzed to determine the highest and lowest row position of the data in region 14-4. This corresponds to the height variation of the top surface of the part perpendicular to the direction of mechanical scan across the width of the camera 14-3. The midpoint of this height variation is calculated and corresponds to height position 14-6 in the camera image and 14-7 in optical depth of field image. Position 14-7 corresponds to the midpoint of the optical depth of field indicated by arrows 14-2.

In general, the optimal focus point is calculated as a function of the depth of field of the optics and the inspection plane of interest, both which are known prior to performing the inspection scan. As stated previously, the system can be programmed to track the top surface, bottom surface or a midpoint between the surfaces if the depth of field is sufficient to keep both surfaces in focus simultaneously as shown by position 9-4 in FIG. 9.

Figure 2:
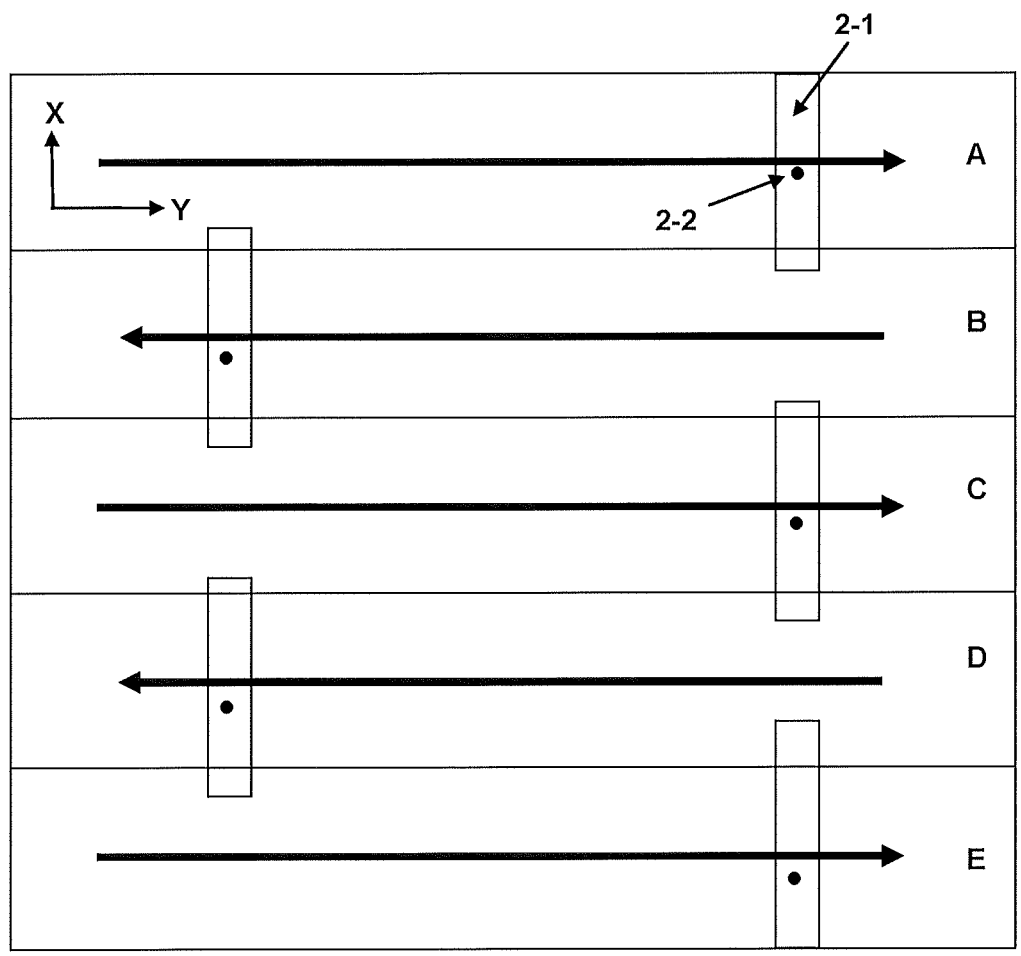
FIG. 2 depicts a prior art autofocus methodology.
Figure 3:
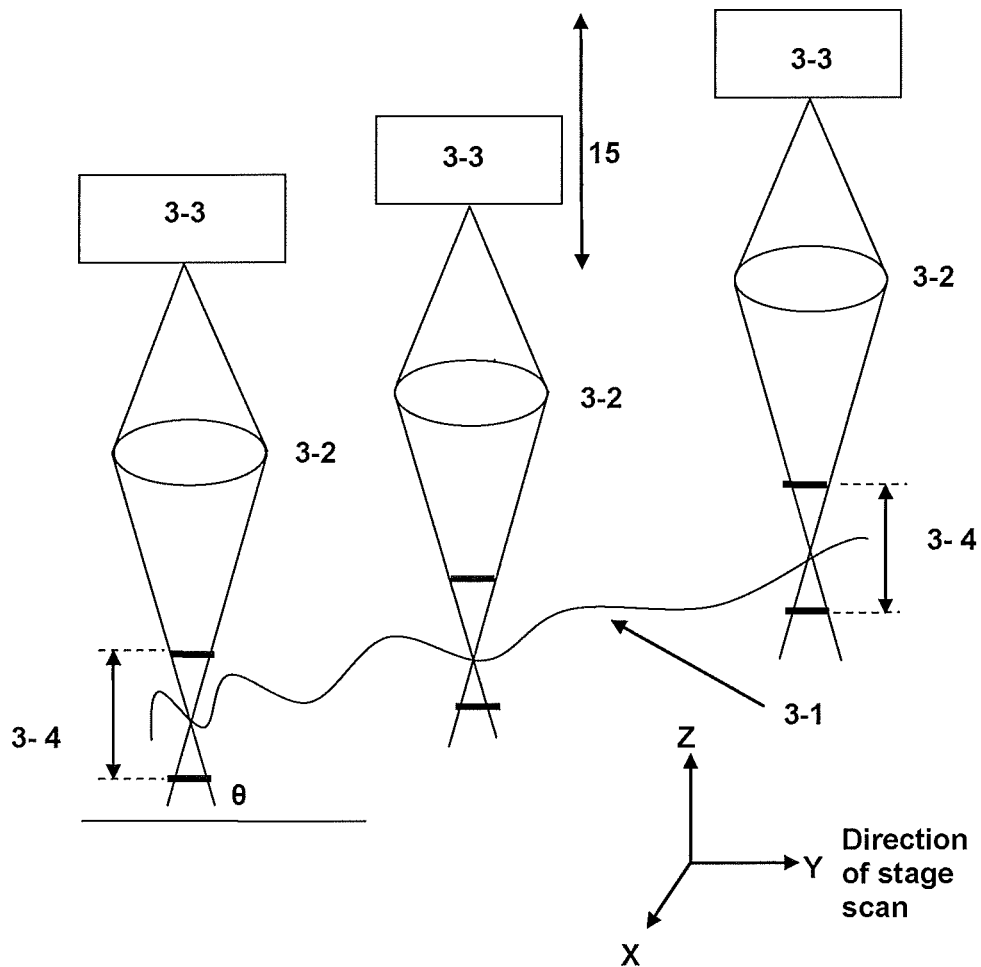
FIG. 3 depicts a part with a wavy portion at an incline.
Figure 4:
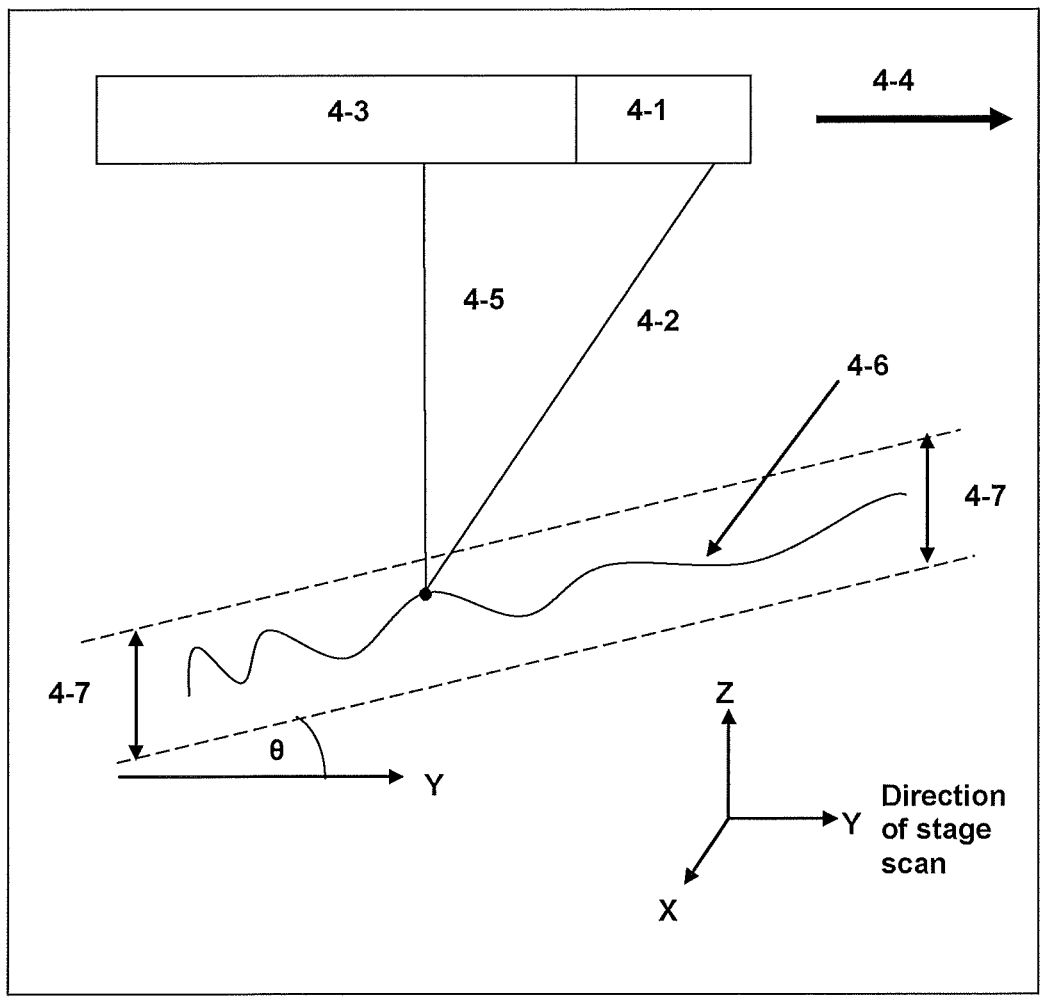
FIG. 4 depicts a prior art optical inspection system that incorporates triangulation.
Figure 5:
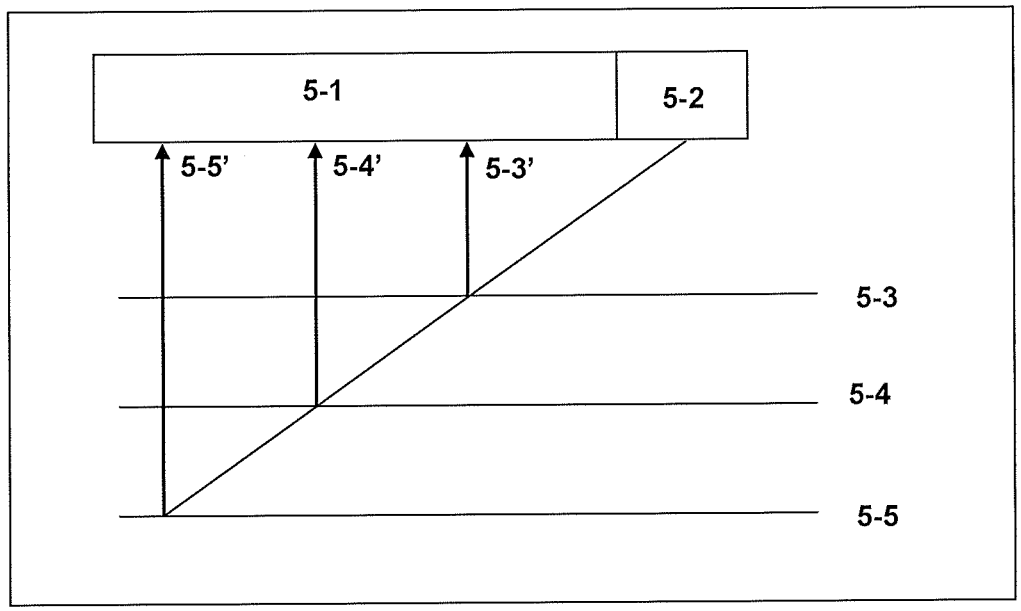
FIG. 5 is useful in understanding this invention.
Figure 6A:
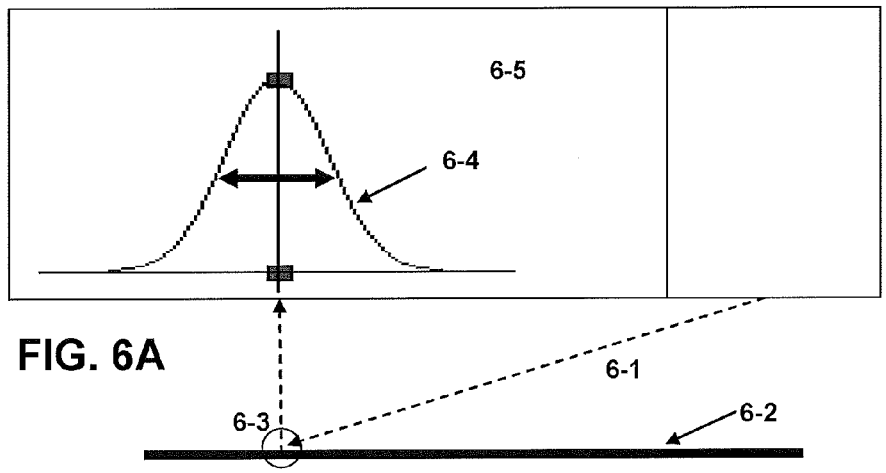
FIG. 6 includes FIGS. 6A, 6B and 6C and is useful in understanding a limitation of prior art optical inspection systems.
Figure 6B:
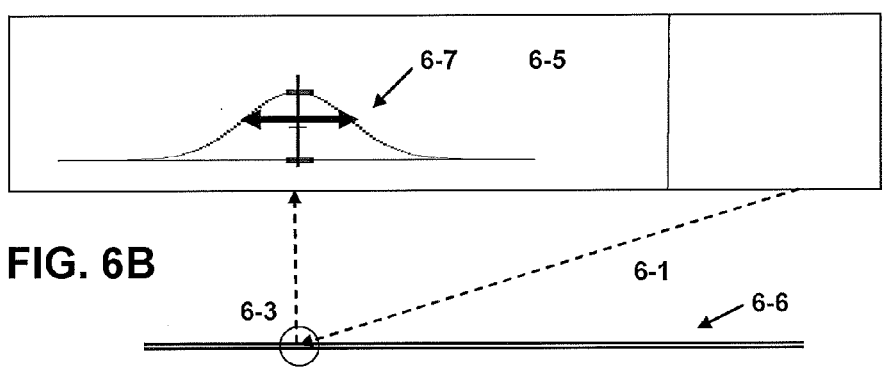
Figure 6C:
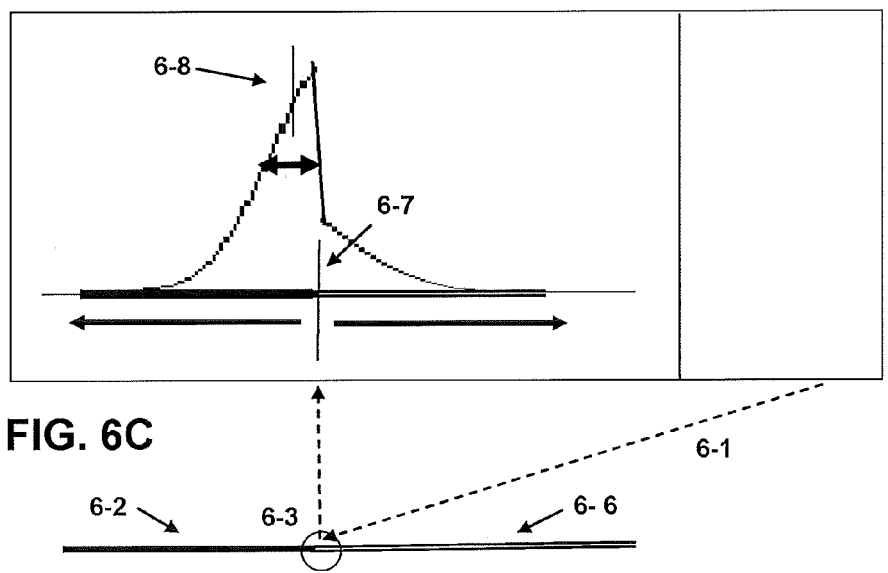
Figure 7:
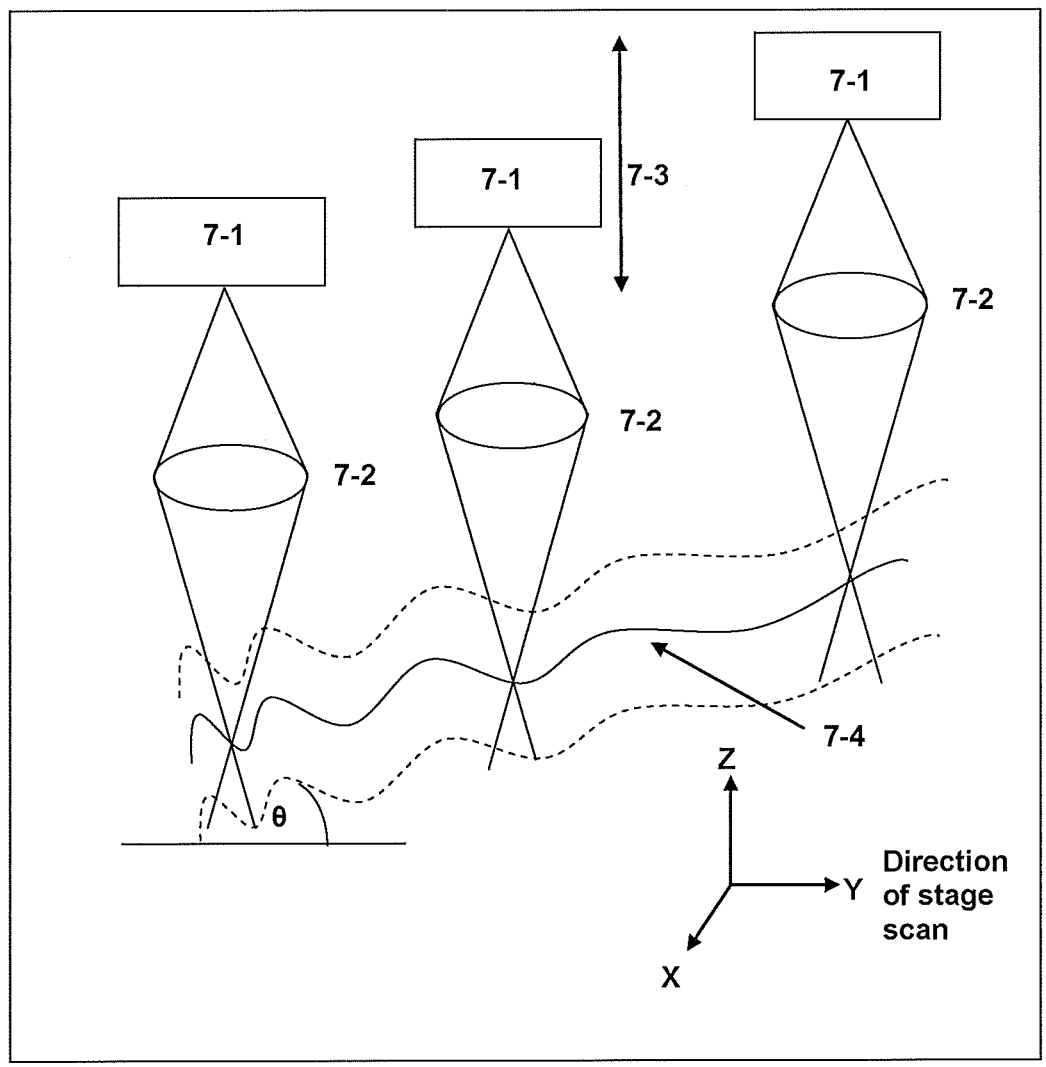
FIG. 7 is useful in understanding another limitation of prior art optical inspection systems.
Figure 8:
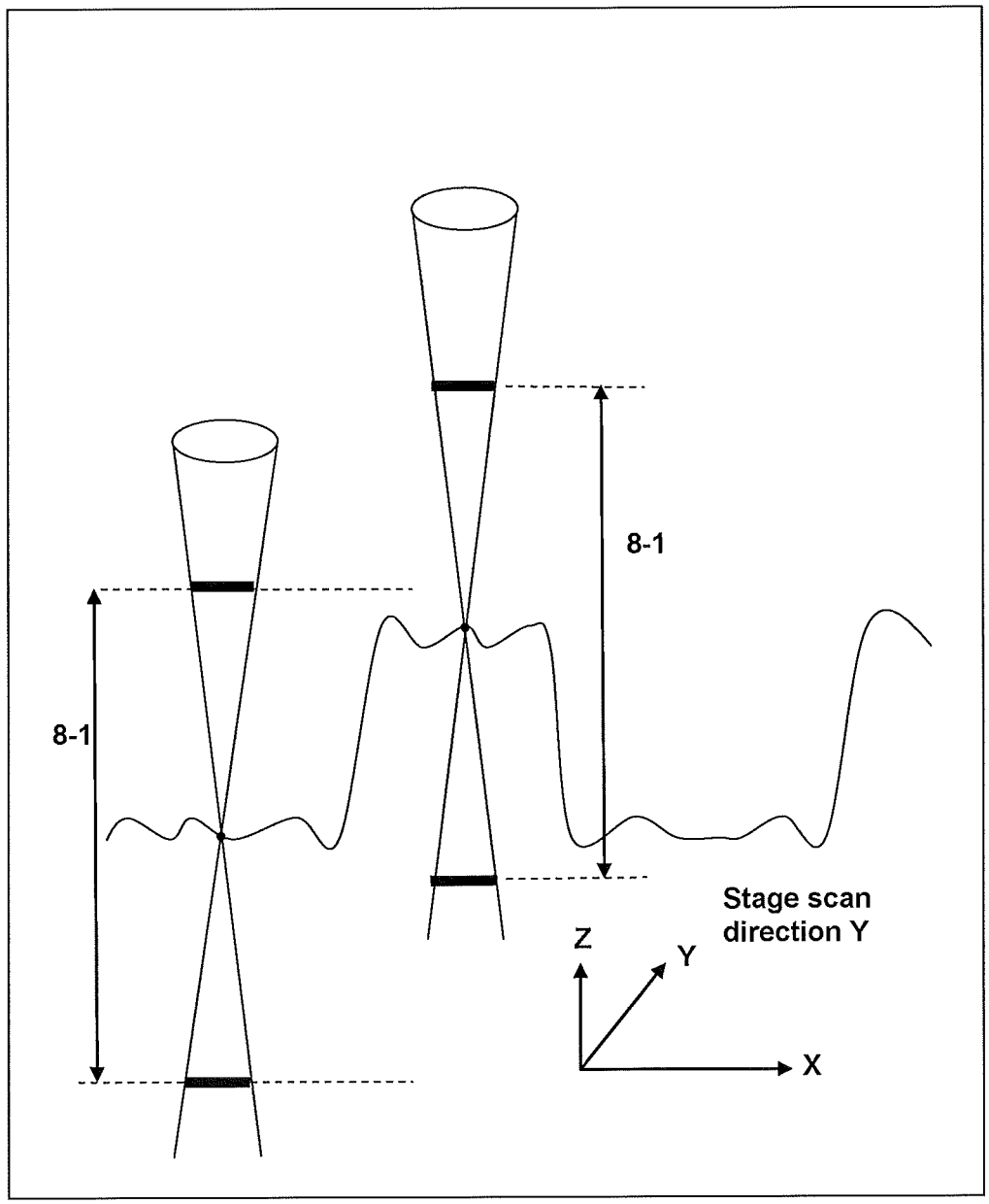
FIGS. 8 through 11 are useful in understanding this invention.

To summarize, as the part is scanned in the Y axis direction, the focus camera 14-3, collects data in the X direction corresponding to the width axis of the inspection camera 2-1 in FIG. 2. The data is analyzed across the entire focus camera to determine a unique single optimal focus point for each different position along the scanning Y axis.

High speed autofocus tracking is essential for quick inspection of such parts. High speed focus calculations and mechanical response is even more essential to achieve real time through the lens focusing To achieve such high speed operation it is advantageous to use as a focus camera 12-13 in FIG. 12A, a camera in which one can selectively pick the camera pixels to read out of the camera, rather than having to read out all the pixels into a storage device and then read the pixels of interest. This saves much time. For example if the focus camera has a total of 1000×1000 pixels ($10^6$ pixels total) and one can determine the location of the top surface of a part by sub-sampling every $5^{th}$ horizontal camera pixel and every other vertical pixel within the top half of the camera. This would reduce the amount of data by a factor 20. Selecting every $5^{th}$ or $N^{th}$ horizontal pixel in the camera image creates specific columns of data. The spacing between such columns is indicated by arrow 14-8 in FIG. 14. Thus, by being able to selectively choose specific regions of interest within the focus camera's field of view, box 14-4 for example, and selectively choosing or sub-sampling pixels within this region greatly decreases the time required to compute the optimal focus positions.

Such a camera made by Photon Focus model MV-D1024E-80-CL or a faster camera with more pixels made by Basler model acA2000-340 km has been used to implement camera block 12-13 in FIG. 12A. This Photon Focus camera contains 1024×1024 pixels, has a spectral response from 350-1000 nm making it capable of operating in the near infrared band and enables reading out of select regions and pixels within the camera. To implement the focus calculation described in this invention, 40,000 pixels have been read out of this camera at a rate of 1000 frames per second. The Basler camera contains 2048 columns×1000 rows and also has a spectral response from 350-1000 nm making it capable of also operating in the near infrared band and enables reading out of select regions and pixels within the camera. To implement the focus calculation described in this invention, 96,000 (pixels have been read out of this camera at a rate of 5000 frames per second. The gain of both focus cameras also is programmable which supports imaging of a wide range of reflective materials and surfaces. A high speed Focus Processor, shown as block 12-19 in FIG. 12A, programs the focus camera parameters over line 12-20 and reads camera pixel data over line 12-21. A Focus Processor 12-19 has been implemented using Stratix programmable logic devices (PLD's) manufactured by Altera Corporation. The Focus Processor 12-19 also communicates with a general purpose computer 12-25, such as an Intel Xenon based computer running Windows XP as an operating system as to enable initial operator setup and control.

During a focus calculation setup operation the Focus Processor 12-19 and or computer 12-25 can adjust both the gain of the focus camera, over line 12-20, and the light intensity of the infrared light source 12-3 over line 12-22. The ability to control both these variables provides the largest possible dynamic range for focusing on either very dim or very bright materials or surfaces.

Figure 1:
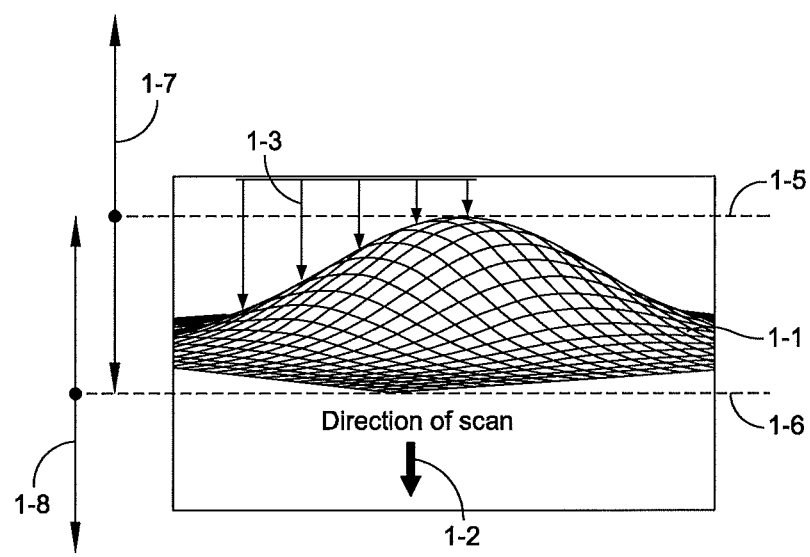
FIG. 1 depicts a portion of a part for inspection with variations in surface height.

Once the optimal focus position has been calculated either the entire optical head indicated by arrow 12-18 is mechanically moved or just imaging lens 12-8 is mechanically moved, or both are moved in some combination to maintain focus. The imaging lens 12-8 can be attached to a precision Z axis motor 12-24 to enable rapid motion in the Z focus axis due to rapid height changes (i.e., high-frequency changes) as shown in FIG. 1. The entire optical head 12-18 can also be attached to a precision motor or may be attached to a holder for the substrate to enable relative motion in the Z axis between the part and the optical head in response to low frequency changes. This may appear when the substrate for the part varies due to a lower frequency warpage. Both motors can be controlled by the Focus Processor 12-19. This system was implemented using a precision linear motor 12-23 produced by Primatics Corporation that moved the entire optical head 12-18. The precision Z axis motor 12-24 that adjusts the image optics relative to the optical head and part for producing such rapid motion is a Piezo electric unit manufactured by PI (Physik Instrumente) L.P. model P-725 PIFOC. This Piezo unit can move the imaging optics +/−200 microns in 50 milliseconds. Another advantage of the through the lens implementation is that focus accuracy and the spatial distance that the focus line pattern moves on the focus camera tracks the optical depth of field of the imaging optics. As depth of field decreases and resolution increases the focus line moves a greater distance on the focus camera for a given change in z height position of the imaging optics. As an example, using the methods and technology described herein, focus was maintained well within a +/−25 micron optical depth of field for imaging optics used to inspect the top surface of parts with height variations within camera images also equaling +/−25 microns in which the size of the parts were up to 500 mm×500 mm which is in the order of sizes of embedded die applications. The entire part was in focus over the entire inspection.

Figure 15:
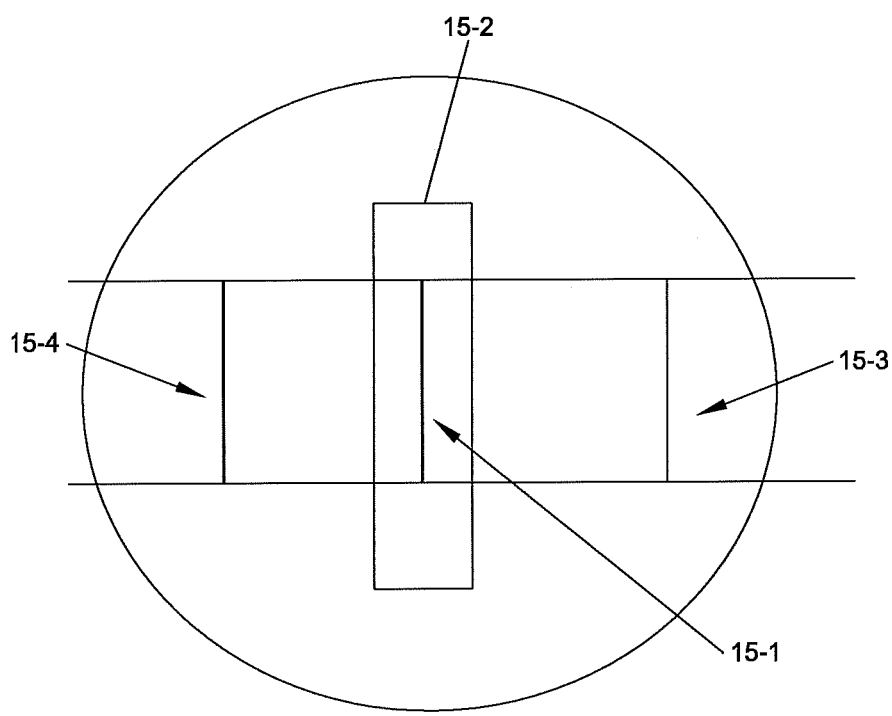
FIG. 15 is useful in understanding the operation of the second embodiment of the apparatus in FIG. 12B.

FIG. 15 depicts the relationship between a focus line 15-1 corresponding to the focus line 12-9 generated by the apparatus in FIG. 12A and the field of view 15-2 for the imaging camera 12-17 wherein the focus line 15-1 is within the field of view 15-2. When the system incorporates such a single focus line 15-2 within the field of view 15-1, in some applications it is possible that by the time the system may move to a newly calculated height the relative positions may have changed producing a following error because the optical head is attempting to measure and move to the same location simultaneously.

In another approach, two focus lines are generated on either side of the inspection camera. FIG. 12B depicts such a two focus-line apparatus which is similar to the apparatus shown in FIG. 12A, but that adds a second illumination source. In this implementation, the optics in the path for the original height measurement beam 12-2 relocates the beam so that it reflects to the left of the inspection camera field of view in FIG. 15 as a scan focus line 15-3. A second optical path 12-30 includes a second illumination source 12-31, a collimating lens 12-32 and a cylinder lens 12-33. Light emanating from the cylinder lens 12-33 reaches the dichroic mirror 12-7 and reflects along a different path to appear as a focus line 15-4 on the other side of the image camera field of view 15-1.

As will now be apparent, when the scanning direction of the apparatus in FIG. 12B is from left to right as shown in FIG. 2 as strip A, the focus beam path 12-30 generates the focus line 15-4 that "leads" the imaging camera field of view 15-1. When the scanning direction of the apparatus in FIG. 12B is from right to left as shown in FIG. 2 as strip B, the focus beam path 12-31 generates the focus line 15-5 that "leads" the imaging camera field of view 15-1. Whereas the field of view of the inspection camera is within region 15-1, the field of view of the focus camera is sufficiently large such that both focus lines 15-4 and 15-5 can be seen by the focus camera. In one direction of travel only rows of data containing information from focus line 12-30 are read out of the camera. In the other scan direction only rows of data containing information from focus line 12-31 are read out of the focus camera. To increase focus camera signal to noise and obtain an even better estimate of height variations in advance of the arrival of the imaging camera located at 15-1, successive rows of scanned data that lie between inspection camera position 15-1 and the location of the focus line can be acquired and processed. Such processing can obtain an average for each height measurement position for a preset number of rows to obtain filtered values that are then used to position the imaging optics for the inspection camera 12-17. Thus, in accordance with this invention, they are provided a variety of approaches for acquiring image lens positioning data.

Figure 16A:
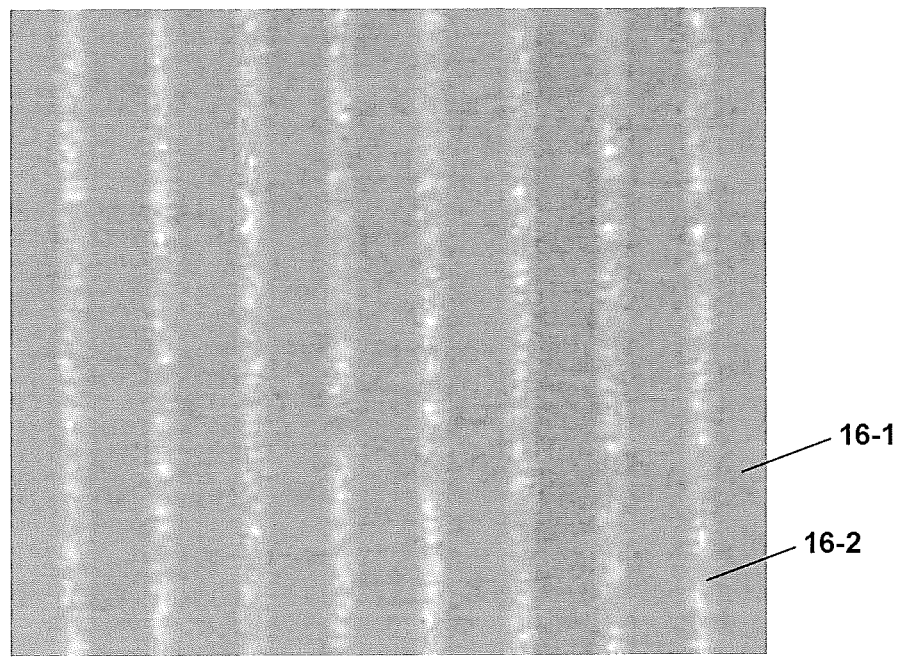
FIGS. 16A and 16B are photographs of inspected images taken by prior art apparatus and apparatus of this invention.
Figure 16B:
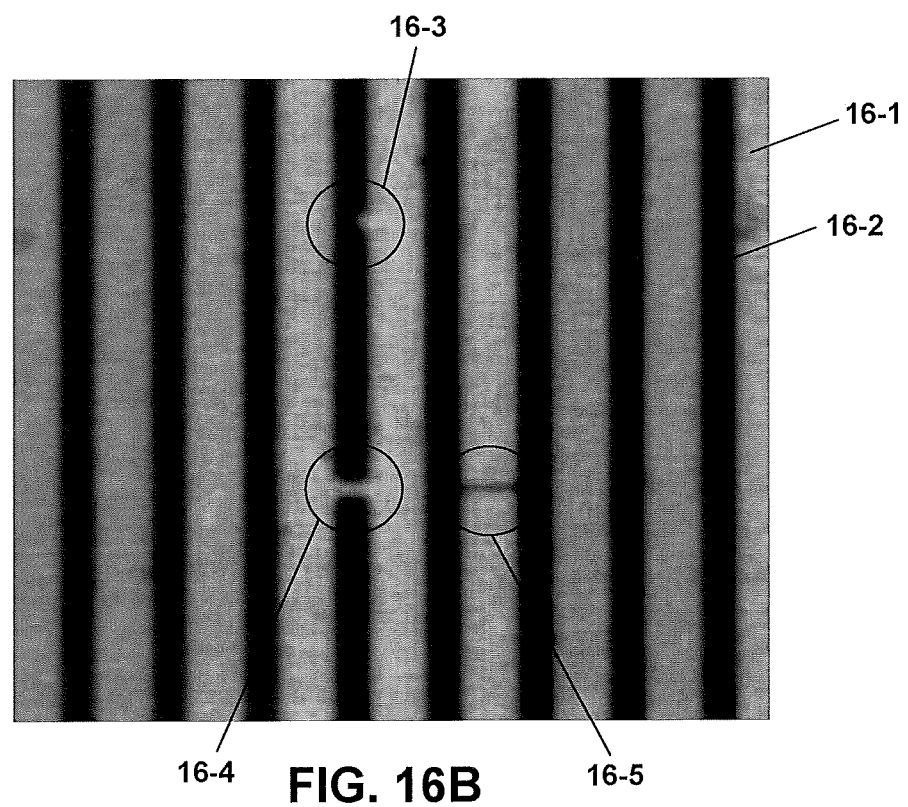

In each of the embodiments of FIGS. 12A and 12B, the focus illumination sources 12-3 and 12-31 operate in the infrared. In the foregoing embodiments, the imaging illumination source 12-14 generates light in the visible spectrum (i.e., white light) for illuminating the part for the imaging cameras 12-17. FIG. 16A depicts an image obtained using the autofocus system of this invention in combination with white light for imaging the part that comprises an opaque organic substrate 16-1 with a plurality of spaced parallel copper conductors 16-2. This is a low-contrast image because the imaging camera 12-17 in FIGS. 2A and 12B receives scattered radiation reflections. FIG. 16B depicts the same part when the imaging camera light source 12-14 comprises a laser with a frequency that will cause the substrate 16-1 to fluoresce. In this configuration, beam splitter 12-5 is replaced with a dichroic filter to reflect the laser and permit returning fluorescent light to reach inspection camera 12-17. In addition a blocking filter 12-26 is inserted in front of lens 12-16 to prevent any reflected laser light from reaching imaging camera 12-17 and insuring only fluorescent light emitted from the organic surface reaches imaging camera 12-17. As the substrate 16-1 is opaque, and as the substrate 16-1 is intact, no fluorescence from any lower layer is received. FIG. 16B shows the resulting fluorescent image with a bright substrate 16-1 and dark conductors 16-2. The improved high contrast image readily allows the identification of defects such as defects 16-3, 16-4 and 16-5. It will be apparent, however, that the use of fluorescence in such devices is limited to the inspection of non-fluorescing conductors on the surface of opaque organic substrates because the autofocus apparatus assumes that all variations in height as measured in the infrared are the result of height variations on the top surface of the organic substrate. If the autofocus apparatus were to used on transparent layers the focus apparatus would not be able to determine which features were on the top layer and could potentially focus on the incorrect layer. It is also important to note that focusing wavelengths not in the infrared band can be used as long as the wavelength of the focusing source is excluded from the range of wavelengths imaged by inspection camera 12-17.

As will now be apparent, autofocus apparatus as disclosed herein meet the objectives of providing accurate focus positions for an imaging camera which assures that the entire image in the image camera's field of view will be in focus. Moreover, the disclosed and other embodiments of this invention can be implemented without departing from the spirit and scope of this invention and can realize any or all of the benefits of this invention. Therefore, it is intent of the appended claims to cover all such variations as come within the true spirit and scope of this invention.

What is claimed as new is:

1. A method for detecting defects at the surface of a part by scanning the part illuminated at a first frequency along a mechanical scan axis with an inspection camera to obtain a plurality of images at a succession of image fields extending perpendicularly to the mechanical scan axis wherein the inspection camera has an objective lens with a fixed working distance and depth of focus and wherein the part is characterized by height variations which define a two-dimensional vertical height profile plane between the part and the objective lens along a camera axis perpendicular to the direction of the mechanical scan, said method automatically focusing the inspection camera on each image field at a calculated focal plane distance to ensure that the entire image is in focus; a calculation of the focal plane distance comprising the steps of:
- A) projecting a line pattern at an inclined angle relative to the surface of the part and perpendicular to the direction of the mechanical scan axis, at a second, non-interfering, frequency through the objective lens onto the part and receiving an image of the line pattern from the surface of the part through the objective lens and projecting this image onto the surface of a two-dimensional focus camera thereby converting the two-dimensional vertical height profile plane created between the part and objective lens along the inspection camera axis perpendicular to the direction of the mechanical scan into a two-dimensional focus height image projected onto the surface of the focus camera for each image field of the inspection camera,
- B) defining a two-dimensional region on the surface of the focus camera such that only those features on the part which are projected onto the defined two-dimensional region of the focus camera will also be in focus on the inspection camera,
- C) analyzing, measuring, and processing the range of heights projected onto the focus camera, including the minimum and maximum heights contained in the projected image and calculating the focal plane distance that keeps the projected surface heights of interest within the spatial region of the focus camera corresponding to an in focus image on the inspection camera, such that all surfaces of interest in the image field of the inspection camera will be within the depth of field of the objective lens and inspection camera, and
- D) adjusting the position of the objective lens to the processed focal plane distance for a given image field such that only that portion of the projected image that lies within a specified region of the focus camera will be in focus on the inspection camera.

2. The method of claim 1 wherein the inspection camera includes a linear charge coupled device.

3. The method of claim 1 wherein the inspection camera includes a linear time delay and integrate charge coupled device.

4. The method of claim 1 wherein the first frequency band is in the visible light band.

5. The method of claim 1 wherein the second frequency is in the infrared band.

6. The method of claim 1 wherein the part includes a material that fluoresces and the first frequency band is in a band that causes the material to fluoresce.

7. The method of claim 1 wherein said measuring includes recording the focal plane distances along the scanning axis.

8. The method of claim 1 wherein during a scanning operation said measuring and processing are completed prior to the acquisition of an image by the inspection camera.

9. The method of claim 1 wherein the images are taken during a scanning operation along a scanning axis and said measuring includes recording height measurements perpendicular to the scanning direction at each of successive locations and said processing includes processing at least one set of the recorded height measurements to calculate a processed focal plane distance.

10. Apparatus for detecting defects at the surface of a part by scanning the part illuminated at a first frequency along a mechanical scan axis with an inspection camera to obtain a plurality of images at a succession of image fields extending perpendicularly to the mechanical scan axis wherein the inspection camera has an objective lens with a fixed working distance and depth of focus and wherein the part is characterized by height variations which define a two-dimensional vertical height profile plane between the part and the objective lens along a camera axis perpendicular to the direction of the mechanical scan, said apparatus automatically focusing the inspection camera on each image field at a calculated focal plane distance to ensure that the entire image is in focus; a calculation of the focal plane distance comprising the steps of:
- A) means for projecting a line pattern at an inclined angle relative to the surface of the part and perpendicular to the direction of the mechanical scan axis, at a second, non-interfering, frequency through the objective lens onto the part and receiving an image of the line pattern from the surface of the part through the objective lens and projecting this image onto the surface of a two-dimensional focus camera thereby converting the two-dimensional vertical height profile plane created between the part and objective lens along the inspection camera axis perpendicular to the direction of the mechanical scan into a two-dimensional focus height image projected onto the surface of the focus camera for each image field of the inspection camera,
- B) means for defining a two-dimensional region on the surface of the focus camera such that only those features on the part which are projected onto the defined two-dimensional region of the focus camera will also be in focus on the inspection camera,
- C) means for analyzing, measuring, and processing the range of heights projected onto the focus camera, including the minimum and maximum heights contained in the projected image and calculating the focal plane distance that keeps the projected surface heights of interest within the spatial region of the focus camera corresponding to an in focus image on the inspection camera, such that all surfaces of interest in the image field of the inspection camera will be within the depth of field of the objective lens and inspection camera, and
- D) means for adjusting the position of the objective lens to the processed focal plane distance for a given image field such that only that portion of the projected image that lies within a specified region of the focus camera will be in focus on the inspection camera.

11. The apparatus of claim 10 wherein said inspection camera includes a linear charge coupled device.

12. The apparatus of claim 10 wherein said inspection camera includes a linear time delay and integrate charge coupled device.

13. The apparatus of claim 10 wherein the first frequency is in the visible light band.

14. The apparatus of claim 10 wherein the second frequency is in the infrared band.

15. The apparatus of claim 10 wherein the part includes a material that fluoresces and the first frequency is in a band that causes the material to fluoresce.

16. The apparatus of claim 10 wherein said measurement means includes means for recording focal plane distances along the scanning axis.

17. The apparatus of claim 10 wherein during a scanning operation said focal plane distance means records height measurements prior to the acquisition of an image by the inspection camera.

18. The apparatus of claim 10 wherein the images are taken during a scanning operation along a scanning axis and said height measurement means includes means for recording height measurements perpendicular to the scanning direction at each of successive locations and said processor means processes at least one set of the recorded height measurements to calculate a processed focal plane distance.

* * * * *